(12) United States Patent
Foster et al.

(10) Patent No.: US 9,980,763 B2
(45) Date of Patent: May 29, 2018

(54) APPARATUS FOR MIXING AND DELIVERING BONE CEMENT

(71) Applicant: SUMMIT MEDICAL LIMITED, Bourton on the Water, Gloucestershire (GB)

(72) Inventors: David Foster, Oxford (GB); Robert Bruns, Oxford-shire (GB)

(73) Assignee: Summit Medical Limited, Gloucestershire (GB)

( * ) Notice: Subject to any disclaimer, the term of this patent is extended or adjusted under 35 U.S.C. 154(b) by 293 days.

(21) Appl. No.: 14/778,062

(22) PCT Filed: Mar. 18, 2014

(86) PCT No.: PCT/GB2014/050847
§ 371 (c)(1),
(2) Date: Sep. 17, 2015

(87) PCT Pub. No.: WO2014/147385
PCT Pub. Date: Sep. 25, 2014

(65) Prior Publication Data
US 2016/0278836 A1    Sep. 29, 2016

(30) Foreign Application Priority Data

Mar. 18, 2013 (GB) .................................. 1304902.8

(51) Int. Cl.
*A61B 17/88* (2006.01)
*B01F 7/00* (2006.01)
(Continued)

(52) U.S. Cl.
CPC ...... *A61B 17/8833* (2013.01); *A61B 17/8819* (2013.01); *A61B 17/8822* (2013.01);
(Continued)

(58) Field of Classification Search
CPC . A61B 17/88; A61B 17/8833; A61B 17/8822; A61B 17/8825; A61B 17/8819
See application file for complete search history.

(56) References Cited

U.S. PATENT DOCUMENTS

| 5,551,778 A | * | 9/1996 | Hauke | ................. | B01F 11/0082 |
| | | | | | 206/222 |
| 2003/0012079 A1 | * | 1/2003 | Coffeen | ............ | A61B 17/8822 |
| | | | | | 366/130 |

(Continued)

FOREIGN PATENT DOCUMENTS

| DE | 102010004342 | 7/2011 |
| EP | 0692229 | 1/1996 |

(Continued)

*Primary Examiner* — Christopher Beccia
(74) *Attorney, Agent, or Firm* — Rutan & Tucker LLP; Hani Z. Sayed

(57) ABSTRACT

A device for mixing bone cement material, the device comprising a mixing body having a chamber, and wherein the mixing body has an open end; a lid arranged to be fitted to the open end; means for mixing bone cement material in the chamber, the means for mixing comprising a rod extending through the lid and into the chamber, wherein the rod has a frangible portion; said lid comprising a cap moveable to a first position covering the frangible portion of the rod, and to a second position revealing the frangible portion.

18 Claims, 11 Drawing Sheets

(51) Int. Cl.
 *B01F 13/00* (2006.01)
 *B01F 15/00* (2006.01)
 *B01F 15/02* (2006.01)
(52) U.S. Cl.
 CPC ...... *A61B 17/8825* (2013.01); *A61B 17/8827* (2013.01); *B01F 7/00291* (2013.01); *B01F 7/00666* (2013.01); *B01F 13/0023* (2013.01); *B01F 15/00506* (2013.01); *B01F 15/0279* (2013.01); *A61B 17/8816* (2013.01); *A61B 2017/8838* (2013.01); *B01F 2215/0029* (2013.01)

(56) References Cited

U.S. PATENT DOCUMENTS

| | | | |
|---|---|---|---|
| 2010/0046315 A1 | 2/2010 | Merkhan et al. | |
| 2013/0223181 A1* | 8/2013 | De Vries | A61B 17/8827 366/150.1 |

FOREIGN PATENT DOCUMENTS

| | | |
|---|---|---|
| EP | 1492476 | 1/2005 |
| WO | WO9522402 | 8/1995 |

\* cited by examiner

APPARATUS FOR MIXING AND DELIVERING BONE CEMENT

CROSS REFERENCE TO RELATED APPLICATION

This document claims the benefit of, and priority to PCT Application Number PCT/GB2014/050847 filed on Mar. 18, 2014 and GB Patent Application Number 1304902.8 filed on Mar. 18, 2013, incorporated herein by reference in its entirety for all purposes.

FIELD OF THE INVENTION

The present invention relates to an apparatus for mixing and delivering bone cement or the like.

BACKGROUND OF THE INVENTION

Orthopaedic bone cement is used throughout the world to secure hip, knee and other metallic prostheses in an appropriate medical position. Also, bone cement can be used to replace and/or repair damaged bone, such as a bone void filling and spinal column with degenerative intervertebral discs by permanently stabilising adjacent vertabrae by fusion.

Bone cement for both joint surgery and bone void filling is generally provided as two or more components, often a powder and a liquid, that, when thoroughly mixed together, form a paste or cement. Thorough mixing of the components is necessary to avoid brittle or "hot" spots. After mixing, the cement generally has to be used quickly before it sets hard.

Bone void filling is used in the repair of osteoporotic bone, typically after fracture, by stabilising the bone and allowing bone growth. In some cases bone growth stimulants are added to the materials to hasten healing. Calcium based sulphates and phosphates materials are typically used. The principles of mixing apply equally to both PMMA bone cement and bone void filling cements.

Bone cement is produced by thoroughly mixing together two components, usually methylmethacrylate monomer liquid and polymethylmethacrylate (PMMA) powder. This type of material is typically used in joint surgery including hips, knees and small joints such as the shoulder, hand and wrist, and foot and ankle.

The mixing is usually carried out using a simple bowl and spatula. The liquid and powder components are put into the bowl and the surgeon or assistant uses a pestle or spatula to thoroughly mix the components. The surgeon then removes the required amount of cement and manipulates it by hand before inserting it into a preformed cavity or applying it to a resected bony surface where the prosthesis is to be positioned. Cement may be applied by hand or may be put into a syringe and applied separately. However, this simple mixing has two major drawbacks.

Firstly, free methylmethacrylate fumes are emitted from the mixture. It is desirable to remove these fumes, or prevent them from escaping into the atmosphere, since they have an unpleasant odour and may be harmful to operating room personnel. The fumes are known to cause nausea and giddiness and are generally objectionable, particularly to the nurses who carry out the mixing. There has also been concern that long term exposure to these fumes results in a more serious health risk. Current employment law relating to occupational health mean medical staff must now be protected against the exposure to hazardous substances.

Secondly, a very high mixing efficiency is required to produce a homogenous cement material. During the mixing process, air is naturally introduced into the mixture since air is inherently existent within the powder and also in and around the mixing vessel. Air bubbles are also produced by the "boiling off" of monomer which occurs during the mixing process. The introduction of air produces a weak cement and, since the joint must usually support a heavy load, it is important to reduce the amount of air in the mixture as much as possible in order to improve the mechanical strength of the cement material.

In order to eliminate as much air as possible from the mixture, desirable for most types of cement, mixing is now preferably carried out in a closed vessel, most preferably under vacuum. This considerably reduces the amount of air in the mixture. Mixing in a conventional bowl and spatula system can produce a product with a porosity value of 20% to 25%. In a vacuum mix, the porosity value is often reduced to levels below 5%.

As mentioned above, calcium phosphates and sulphates can be used as another type of bone cement material, which does not necessarily need to be mixed in a vacuum. Conventionally, this type of bone growth stimulant is prepared in paste form and is delivered to an application site.

Several devices for mixing the cement are available. Some of these are in the form of hand-held mixing bowls as mentioned above. WO 93/10892 describes an improved bowl mixer. The substances to be mixed are placed by means of a rotating paddle extending into the bowl to which a vacuum is applied. The substances are mixed by means of a rotating paddle extending into the bowl which is rotated manually by means of a handle extending through the lid of the bowl. In some applications, an example of which is disclosed in WO 93/10892, bowl mixing is favoured. Many surgeons prefer to "hand pack" the cement. Bowl mixing tends to be preferred by nurses who are used to the convenience of mixing in this vessel; a bowl is easier to use and it is important that nurses feel confident since timing is very crucial and the mixture must be "right first time". Many surgeons also tend to prefer bowl mixers because they can easily take samples of the cement from the bowl at any time to determine the progress of polymerization as it is crucial that the mixture does not begin to set before it is applied.

However, in some applications, it is preferable or necessary to apply the mixed cement to the bone by means of a syringe. Indeed some surgeons, particularly in Europe, prefer syringe-type application to "hand packing". If the cement is mixed in a bowl, it must then be transferred to a dispensing syringe which can be messy and time consuming and may expose the mixture to more air entrapment. This problem has been overcome by combining a mixing chamber with a syringe. Although advantages can be obtained with a simple closed mixing chamber/syringe combination, creating a vacuum can provide additional advantages. For example, EP 0178658 discloses a device for mixing bone cement comprising a mixing container connected to a feed device. A vacuum source may be connected to the feed device for mixing the substances under vacuum. This device has proved to be a very efficient mixing and transfer system and eliminates the need to transfer the mixed cement from the mixing bowl to a syringe.

However, the mixing paddle of EP 0178658 is rotated by a rotary electric drive motor. This makes the device costly and space consuming and requires specialist and time-consuming installation. The device is not easily portable and its use is, therefore, not particularly flexible.

U.S. Pat. No. 4,758,096 and U.S. Pat. No. 3,606,094 also disclose bone cement mixers in which the cement is mixed in the dispensing vessel. In U.S. Pat. No. 4,758,096, the mixing is effected manually by means of a "masher" plate-type agitator. The masher plate is attached to a shaft attached to a handle. The agitator is movable in the chamber both axially and rotatably to permit mixing of the cement by the user moving the handle vertically and rotatably.

In the device of U.S. Pat. No. 3,606,094, the mixing element comprises an elongate conduit having paddle projections. The paddles are rotated by a rotating motor or by hand.

EP 0744991 discloses a bone cement mixer in which the mixing chamber forms the body of a dispensing syringe wherein a nozzle can be attached to one end of the mixing chamber so as to dispense the bone cement.

GB 2411849 discloses an apparatus for mixing bone cement and discharging the mixed bone cement from a mixing container into a discharging device such as a syringe or syringes.

Another product on the market that provides a mixing and dispensing device is the HiVac™ 7 (provided by Summit Medical Ltd., see http://www.summit-medical.co.uk/product/hivac7.html). This device allows for mixing, e.g. biologics, in a mixing chamber. The HiVac™ 7 provides a mixing rod having a diameter of 8 mm. Once the mixing phase is complete, a cap can be lifted from one end to reveal a "luer" connection to which a nozzle can be attached. The mixing chamber then also acts as a dispensing chamber and the bone cement can be dispensed through the nozzle.

The bone cement mixing and dispensing devices discussed above have the advantage of providing an apparatus that both mixes and dispenses bone cement material.

Generally, these mixing apparatuses discussed are made to hold a standard volume of cement of 40 cc or more in the mixing and dispensing chambers. Sometimes, however, there is a need for only a small amount (e.g. 10 cc) of cement, for example for smaller joints such as ankles etc., where a volume of 0.5-20 cc, for example, is needed; or for a combination of calcium based sulphates and phosphates. The bulky nature of chambers having, say, 40 cc volume is not easily maneuvered in a smaller target site (for example, ankle joints etc.). Also, the cement components are expensive and use of a greater volume than needed is wasteful and costly. Simply reducing the size of the apparatuses discussed above causes the components therein to become weak and to easily break. For example, simply reducing the size of the components shown in the HiVac™ 7, and particularly the rod, makes these components weak and prone to breaking. There is therefore a need for a device that can cope and assist in treatment at smaller target sites.

Further, optimum mixing occurs in the above devices when the chambers are mostly full—e.g. ~80% full. When a chamber is ~80% full, this allows for a mixer paddle or disc to push through the material and have the resistance from the bone cement material, caused by the material being compressed against the chamber bottom to push the material through the paddle or disc. As the paddle or disc is then returned through the chamber, the material is again pushed through the paddle or disc by resistance. However, if the devices discussed above were to be used for treatment in smaller target sites, it would be necessary to use a smaller amount of bone cement material that would be less than the volume of the chambers discussed above. Simply providing a smaller amount of bone cement material into a chamber with, say, 40 cc volume, or more, has disadvantages. For example, if the chamber were only ~40% full, the material simply clings to the paddle or disc until the paddle or disc hits the bottom of the chamber where it would be pushed through the paddle. Before mixing the material again, the paddle or disc has to travel ~60% of the chamber, which does not provide efficient and optimum mixing. Therefore, there is a need for a device that provides adjustable volumes in the chamber to allow for a range of volume of bone cement material.

The present invention aims to overcome the above-mentioned problems. Of course, several types of bone cement material have been discussed above, but the present invention is not so limited to these types of bone cement material. The present invention aims to provide a device for known types of bone cement material and bone cement material that may be developed in the future.

SUMMARY OF THE INVENTION

In one aspect of the present invention, there is provided a device for mixing bone cement material, the device comprising:
a mixing body having a chamber, and wherein the mixing body has an open end;
a lid arranged to be fitted to the open end;
means for mixing bone cement material in the chamber, the means for mixing comprising a rod extending through the lid and into the chamber, wherein the rod has a frangible portion;
said lid comprising a cap moveable to a first position covering the frangible portion of the rod, and to a second position revealing the frangible portion.

In a preferred embodiment, the mixing rod can be moved vertically and/or rotatably in the chamber to assist in mixing the bone cement material. In a preferred form, the means for mixing the bone cement material comprises a 'mashing' or paddle portion to assist in the mixing of the bone cement, in the chamber. The 'mashing' or paddle portion can take the form of a 'masher' paddle or a flat-type paddle, and, most preferably, a paddle portion extending radially from the rod.

In a preferred embodiment, a lid is provided at an open end of the mixing body. The lid preferably has a moveable cap that can move to a first position to cover a frangible portion of the rod. When the cap is covering the frangible portion of the rod, the rod is advantageously reinforced against snapping whilst the user is mixing the bone cement in the chamber.

In a further embodiment of the present invention, there is provided means for securing the cap in the first position. This allows for the cap to be secured in a position that covers the frangible portion of the rod so as to reinforce the rod during the mixing phase. In a preferred embodiment, the means for securing the cap in a first position is a removable clip.

In preferred embodiments of the present invention, the mixing body chamber and plunger are preferably cylindrical, and most preferably circular cylindrical.

In a preferred form of the present invention, the lid comprises an inner cap and a movable outer cap. In a preferred embodiment, the inner cap is attached to the open end of the chamber and the outer cap is movable relative to the inner cap. This allows for the open end of the chamber to remain closed during the mixing phase, but to also allow for the rod to be reinforced by the outer cap when this is moved into the first position.

In a preferred form, the frangible portion is a weakened or snap portion, preferably formed by a slight indent or notch provided in the rod. This allows for the user to snap the rod after the mixing phase.

The device is preferably used for mixing and dispensing bone cement material. In a further embodiment of the present application, the mixing body preferably has a second open end. In a preferred form, the mixing body has means for dispensing the cement located at the second open end to assist in dispensing the bone cement material after the mixing phase. Preferably, the means for dispensing the bone cement material is a plunger movable by the application of force through the chamber.

Preferably, the inner cap has a delivery port that allows for bone cement material to be dispensed after the bone cement material has been mixed. In a preferred embodiment, the outer cap has a protrusion extending towards the delivery port of the inner cap so that it can be introduced into the delivery port. Advantageously, the protrusion blocks the delivery port such that no bone cement material can escape. In a preferred form, the delivery port of the inner cap includes a luer port so as to receive a nozzle for dispensing the bone cement material.

Preferably, the mixing or paddle portion of the rod is shaped so as to be engaged by the protrusion of the outer cap such that, when the outer cap is moved down to fit over the inner cap, the protrusion pushes the paddle portion to the side of the chamber. Advantageously, this ensures that the paddle portion is not occluding the delivery port of the inner cap.

In another aspect of the present invention, there is provided a device for mixing bone cement material, the device comprising:
a mixing body having a chamber, and wherein the mixing body has a first end and a second end;
a lid arranged to be fitted to the first end;
means for mixing bone cement material in the chamber, the means for mixing comprising a rod extending through the lid and into the chamber;
means for dispensing bone cement material from said mixing body attached to a second end of the mixing body, wherein the means for dispensing the bone cement material is a plunger movable by the application of force through the chamber, said plunger provided to set an adjustable volume in the chamber prior to mixing;
said device further comprising:
means for positioning the plunger between the first and the second end of the mixing body to define a volume of the chamber; and
means for maintaining the position of the plunger so as to maintain the volume of the chamber during mixing.

The means for positioning the plunger between the first and the second end of the mixing body advantageously allows the user to define a volume of the chamber of the mixing body. Therefore, in this embodiment of the present invention, the user can adjust the volume of the chamber for an amount of bone cement material that is necessary for a particular type of surgery.

There is also provided means for maintaining the position of the plunger so as to maintain the volume of the chamber during mixing. Advantageously, this allows the user to first adjust the amount of volume in the chamber and to then set the volume within the chamber so that the user can then mix the bone cement material for a particular volume.

Preferably, the means for positioning the plunger and the means for maintaining the position of the plunger comprises a screw thread arranged on an outer surface of the plunger, and a nut having a screw thread to be received by the screw thread arranged on the outer surface of the plunger, the nut further having a recess having a screw thread to be received by a screw thread located at the second end of the mixing body. This allows for the user to first position the plunger within the chamber and then to securely screw a nut to the mixing chamber such that the plunger is maintained in a position between the first end and the second end of the mixing body during the filling and mixing phases. This then advantageously allows for the user to adjust the volume for a particular amount of bone cement material that is necessary for a particular type of surgery.

The features of the second aspect, relating to the adjustable mixing volume, are also advantageous for the first aspect of the invention.

In a preferred embodiment, for both aspects, there is also provided a base that is adapted to receive the plunger to stabilise the device during a mixing or filling phase.

Preferably, the mixing rod has a handle or knob located on the end so that the user can easily move the rod vertically and/or rotatably.

In a preferred embodiment of the present invention, the volume of the chamber is between 0-15 cc.

Preferably, the outer cap can be lifted a distance away from the inner cap of between 2-3 mm.

In a preferred form, the diameter of the rod is 4 mm.

In a further embodiment of the present invention, there may be provided a vacuum port located on the lid so as to receive a vacuum pump in the chamber. The vacuum pump advantageously creates a vacuum in the chamber.

In another aspect of the present invention, there is provided a method of mixing bone cement material, said method having the steps of:
providing bone cement components in a mixing chamber of a mixing device;
fitting a lid to an open end of the mixing chamber to close the chamber;
mixing bone cement material using a rod extending through the lid and into the chamber of the mixing device, wherein the rod has a frangible portion; said method characterised by
positioning the lid in a first position so as to reinforce the frangible portion from breakage during mixing;
positioning the lid in a second position so as to reveal the frangible portion; and
snapping the rod at the frangible portion.

In this embodiment, the method of mixing the bone cement material allows the user to mix the bone cement material and also allows for the frangible portion of the rod to be reinforced during mixing.

In a preferred form, the steps of positioning the lid to reinforce the frangible portion comprises providing an outer cap and an inner cap on the lid and preferably moving the outer cap away from the inner cap to a first position. This advantageously allows for the outer cap to cover the frangible portion during mixing.

Preferably, the outer cap can be removed after the mixing phase to reveal a delivery port located on the inner cap so that the user can dispense the bone cement material. In a preferred embodiment, the delivery port includes a luer port that can receive a nozzle so as to assist in the dispensing of the bone cement material.

In a further aspect of the present invention, there is provided a method of mixing bone cement material, said method having the steps of:

setting a volume of a chamber of a mixing device with a plunger, said plunger movable through the chamber with the application of force between a first and a second end of the mixing device;

maintaining the position of the plunger so as to maintain the volume of the chamber during mixing;

mixing the bone cement material in the chamber of the mixing device.

In this embodiment, the method allows the user to adjust the volume of the chamber of the mixing body. This advantageous when an amount of bone cement material different to the total volume of the chamber is needed for a particular type of surgery. The volume can then be adjusted by the user and maintained for use during the filling and mixing phase.

In a preferred form, the steps of setting the volume and maintaining the set volume comprises providing a screw thread arranged on an outer surface of the plunger and providing a nut having a screw thread to be received by the screw thread arranged on the outer surface of the plunger, the nut further having a recess having a screw thread to be received by a screw thread located at the second end of the mixing body. This advantageously allows the user to screw the nut onto the second end of the mixing body.

In one embodiment of the present invention, and when the bone cement material is ready to be dispensed, the user can unscrew the nut from the second end of the mixing body and the plunger can be axially moved through the chamber to push the bone cement material out through a delivery port located on the lid.

In an alternative embodiment of the present invention, and when bone cement material is ready to be dispensed, the user can rotate a second end of the plunger through the screw thread provided on the nut to axially move the plunger through the chamber. This advantageously provides a greater force when dispensing the bone cement material through a delivery port and is particularly advantageous for viscous bone cement material.

In another embodiment of the present invention, a vacuum can be created in the chamber by attaching a vacuum pump to a vacuum port on the lid.

Exemplary embodiments of the present invention will now be described, by way of example only, with reference to the figures.

BRIEF DESCRIPTION OF THE DRAWINGS

FIG. 7b shows a cross-sectional view of the cap as shown in FIG. 6a.

DETAILED DESCRIPTION OF THE INVENTION

Figure 1:
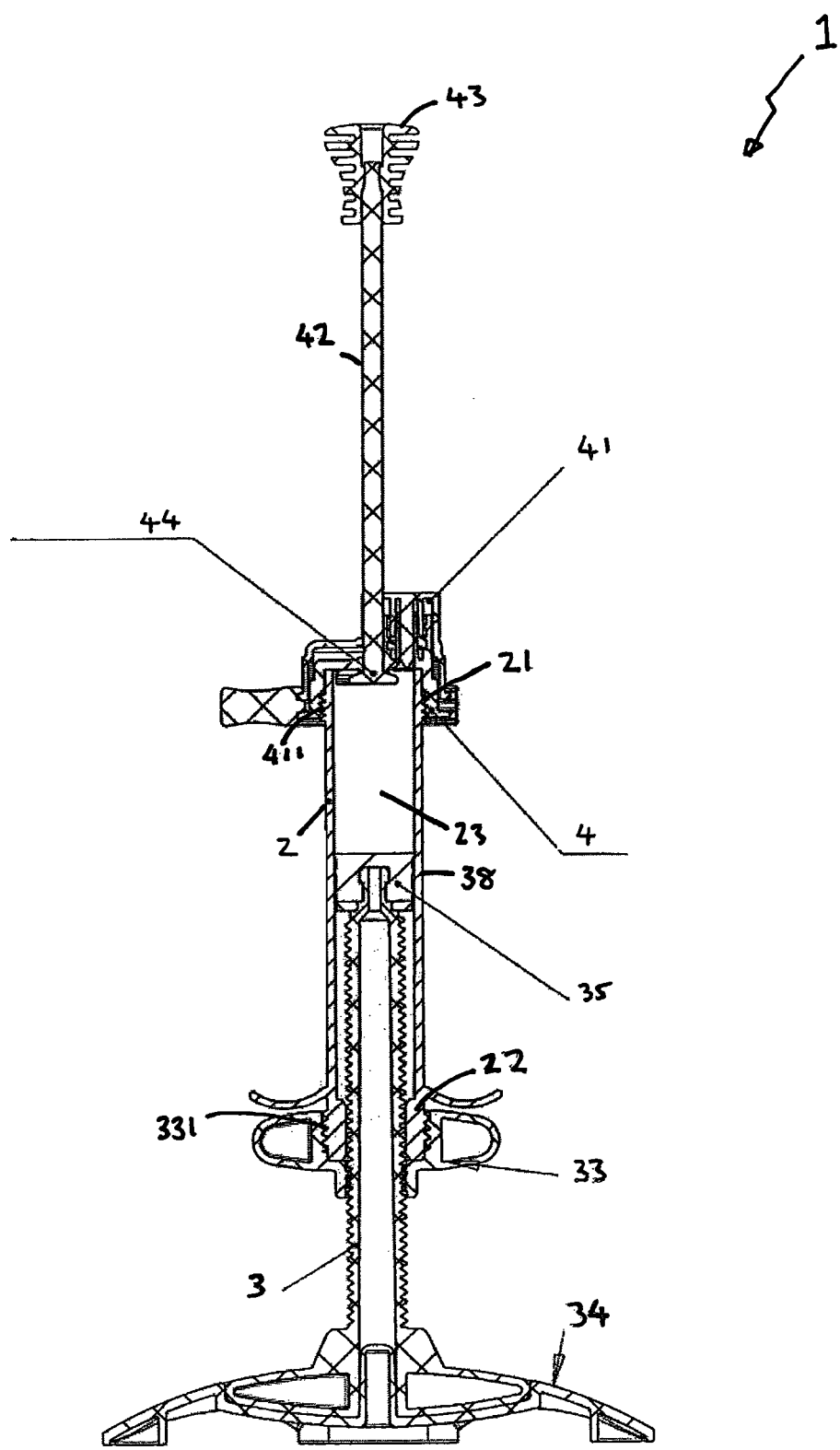
FIG. 1 shows a bone cement mixing and dispensing device in accordance with an embodiment of the present invention.

FIG. 1 shows a complete assembly of a bone cement mixing and delivery device 1 in accordance with an embodiment of the present invention. The bone cement and delivery device 1 can be used to mix and deliver bone cement. As can be seen in FIG. 1, there is provided a mixing/dispensing body 2 having a chamber 23 for receiving bone cement material (not shown). The mixing/dispensing body 2 has a first open end 21 and a second open end 22. The mixing/dispensing body 2 is preferably cylindrical, and more preferably circular cylindrical. However, the mixing/dispensing body 2 may take other forms.

As shown in FIG. 1, there may also be provided an inner cap 411 and an outer cap 41 (described in more detail below) located at, and releasably fastened to, the first open end 21 of the mixing/dispensing body 2.

Also, there may be provided a plunger 3 having a first end 31 and a second end 32, as shown in FIG. 1. The first end 31 of the plunger 3 may include a piston 35 that can be introduced into the mixing/dispensing body 2 at the second open end 22. The piston 35 is preferably flush with an inner surface of the mixing/dispensing body 2. The plunger 3 may have a handle or knob on the second end 32 to assist the user in using the plunger 3. The plunger 3 is preferably cylindrical, and more preferably circular cylindrical. However, the plunger 3 may take other forms.

As shown in FIG. 1, there may also be provided a rod 42 to assist in mixing the bone cement material. The rod 42 may movably extend through openings (not shown) of the inner cap 411 and outer cap 41. The rod 42 has a first end 43 and a second end 44. At the second end 44 of the rod 42, in the mixing/dispensing chamber 23, is provided a 'mashing' or paddle portion 44 to assist in mixing the bone cement material. In a preferred embodiment, the diameter of the rod is between 2-5 mm, and is preferably 4 mm in diameter.

A base 34 may be provided, as shown in FIG. 1. The base 34 may be adapted to receive the second end 32 of the plunger 3 to stabilise the mixing/dispensing device 1 during a mixing or filling phase.

Figure 2:
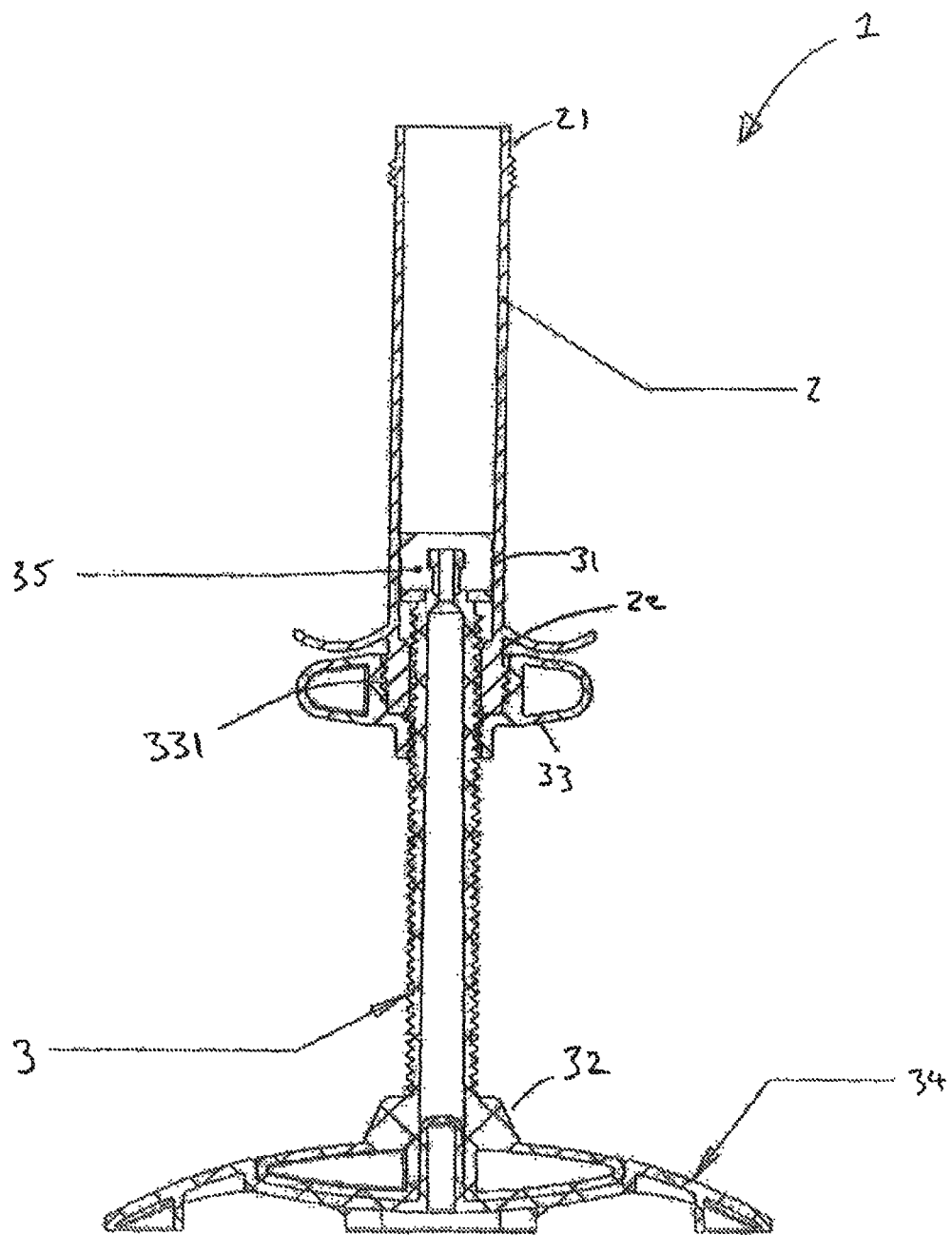
FIG. 2 shows an enlarged portion of the bone cement mixing and dispensing device shown in FIG. 1 prior to delivery of the material to be mixed.
Figure 3:
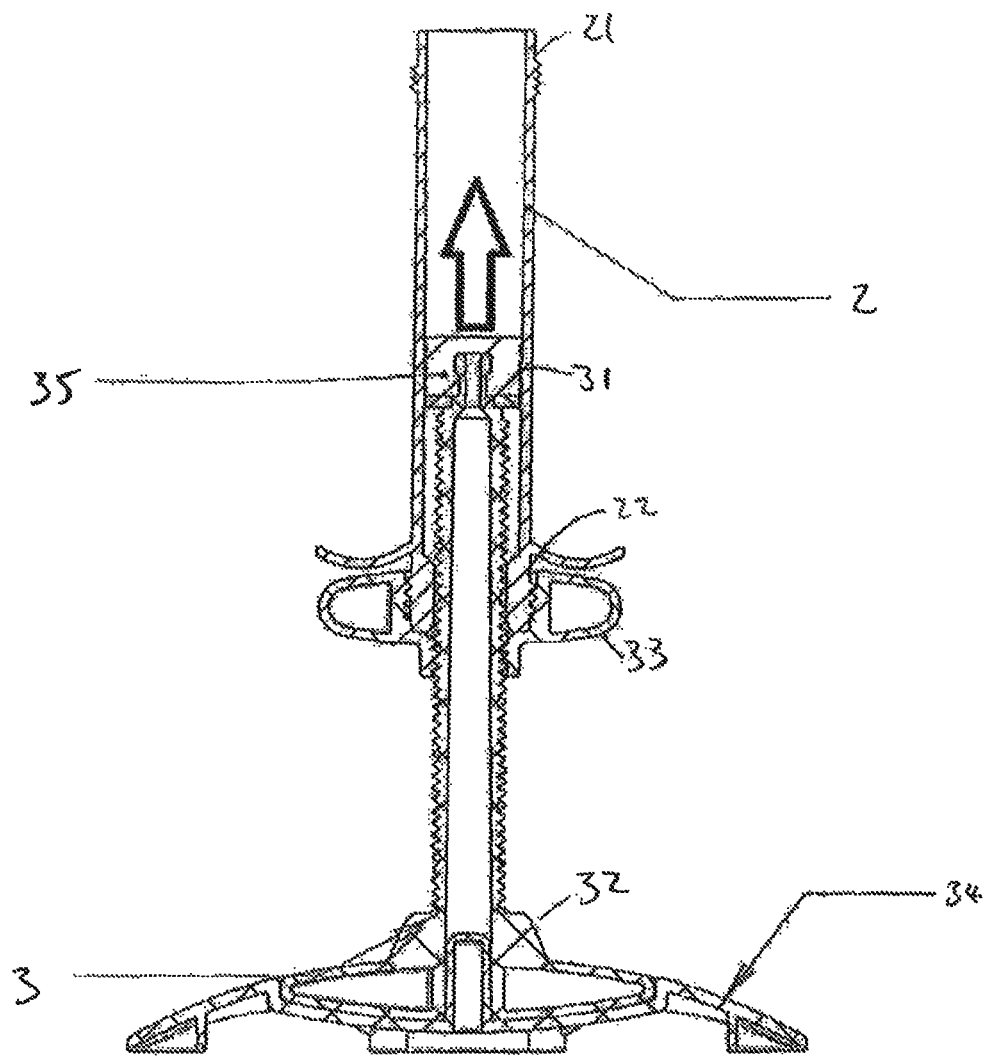
FIG. 3 shows an enlarged portion of the bone cement mixing and dispensing device shown in FIG. 1, in use, prior to delivery of the material to be mixed.

As can be seen in FIGS. 1, 2, and 3, the first end 31 of the plunger 3 can be received by the second open end 22 of the mixing/dispensing body 2. In this arrangement, the piston 35 is, therefore, introduced into the mixing/dispensing body 2 and is flush with an inner surface of the mixing/dispensing body 2. The plunger 3 has, on its outer surface, a screw thread extending from the first end 31 to the second end 32. A nut 33 is located on the screw thread of the plunger 3. The nut 33 includes a recess 331 having a screw thread to fasten to a screw thread located on the outer surface of the second end 22 of the mixing/dispensing body 2. In this arrangement, the piston 35 can be introduced into the second open end 22 of the mixing/dispensing body 2 and can be moved, in a longitudinal direction (shown by the arrow in FIG. 3), through the mixing/dispensing body 2 to provide a specific volume required in a mixing/dispensing chamber 23. The piston 35 can then be held in place by screwing the nut 33 on to the screw thread located on the outer surface of the second end 22 of the mixing/dispensing body 2. This then provides a volume within the mixing/dispensing chamber 23. In a preferred embodiment, the volume of the chamber can be between 0-15 cc.

Once the volume has been set by the user with the technique discussed above, bone cement material is introduced into the first open end 21 of the mixing/dispensing body 2, e.g. through a funnel (not shown).

Either before or after the bone cement material has been introduced into the mixing/dispensing chamber 23, the second end 32 of the plunger may be positioned, and held, in a recess of a base 34. The base 34 assists in keeping the bone cement mixing and delivery device 1 still during the filling and/or mixing phase.

Figure 4:
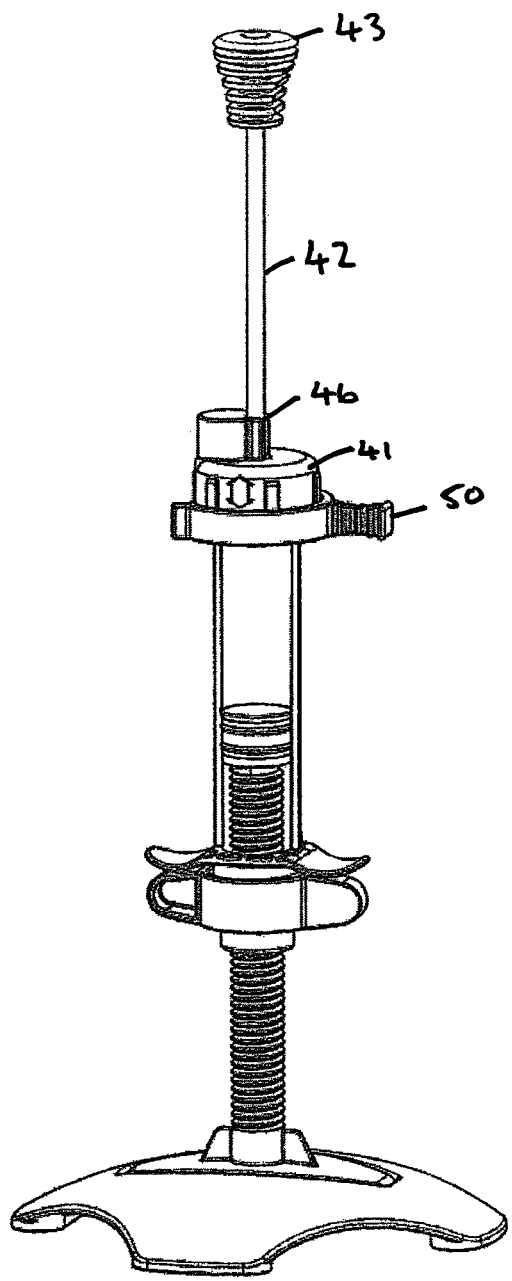
FIG. 4 shows the bone cement mixing and dispensing device of FIG. 1 pre-mixing or during the mixing phase.

Referring now to FIGS. 1 and 4, the lid 4 is now described. After the bone cement material has been introduced into the mixing/dispensing chamber 23, the lid 4 is fitted over the first open end of the mixing/dispensing body 2. The lid has an outer cap 41 and an inner cap 411. The inner cap 411 may have a recess having a screw thread thereon which can mate with a screw thread located on the outer surface of the first open end 21 of the mixing/dispensing body 2. The outer cap 41 can fit over the inner cap 411 and is axially movable relative to the inner cap 411. The lid 4 can be attached to the mixing/dispensing body 2 by mating the screw thread of the inner cap 411 with a screw thread located on the outer surface of the first end 21 of the mixing/dispensing body 2. Other means could be provided to fasten the lid to the chamber.

The outer cap 41 and the inner cap 411 include an opening (not shown) through which a rod 42 moveably extends. At the second end of the rod 42, in the chamber, is provided a 'mashing' or paddle portion 44 to assist in mixing the bone cement material in the mixing/dispensing chamber 23. The rod 42 extends from the paddle portion 44 and through the opening of the outer cap 41 and inner cap 411 to a first end 43. The 'mashing' or paddle portion 44 could be radially extending arms (not shown) from the rod 42 or a 'masher' paddle, or a flat-type paddle portion. Other types of 'mashing' or paddle portions could be used.

In use, the outer cap 41 is lifted a distance away from the inner cap 411 and the first end 21 of the mixing/dispensing body 2. In a preferred embodiment, the outer cap 41 is lifted away by a distance of between 2-3 mm. In order to maintain the distance between the outer cap 41 and the inner cap 411, a clip 50 may be attached around the circumference of the inner cap 411 and/or the outer cap 41. The clip 50 therefore holds the outer cap 41 in place during the mixing phase. The outer cap 41 may also include a reinforcing portion 46 that protrudes from the hole in which the rod 42 extends through. The reinforcing portion 46 provides support to the rod 42 during the mixing phase so that the rod 42 does not snap or break.

The mixing phase is achieved by a user axially and/or rotatably moving the rod 42 so that the paddle portion 44 mixes the bone cement material in the mixing/dispensing chamber 23. The first end 43 of the rod 42 may be provided with a handle or knob 43 to assist the user in mixing the bone cement material.

Figure 5:
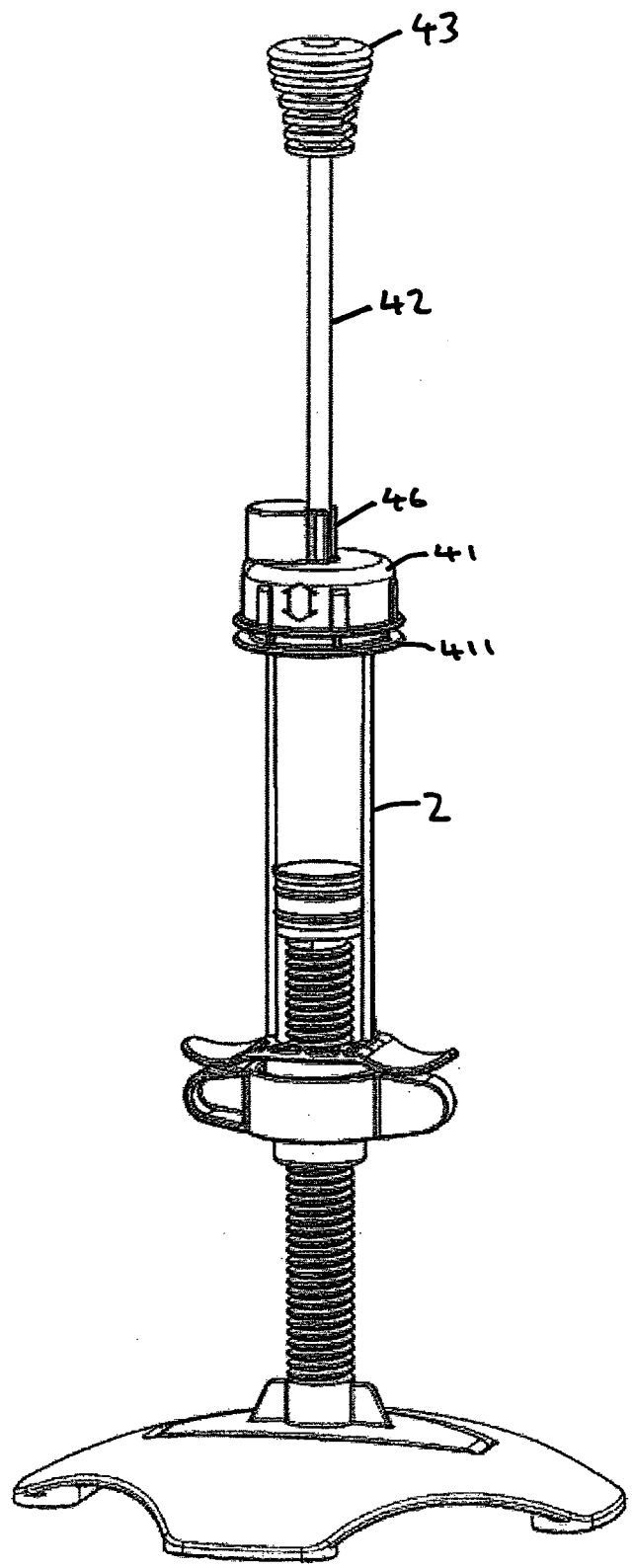
FIG. 5 shows the bone cement mixing and dispensing device of FIG. 1 prior the mixing phase.

As is shown in FIG. 5, when the clip 50 is removed from the outer cap 41 and/or inner cap 411, the outer cap 41 is axially moveable relative to the inner cap 411 and the mixing/dispensing body 2.

Figure 6:
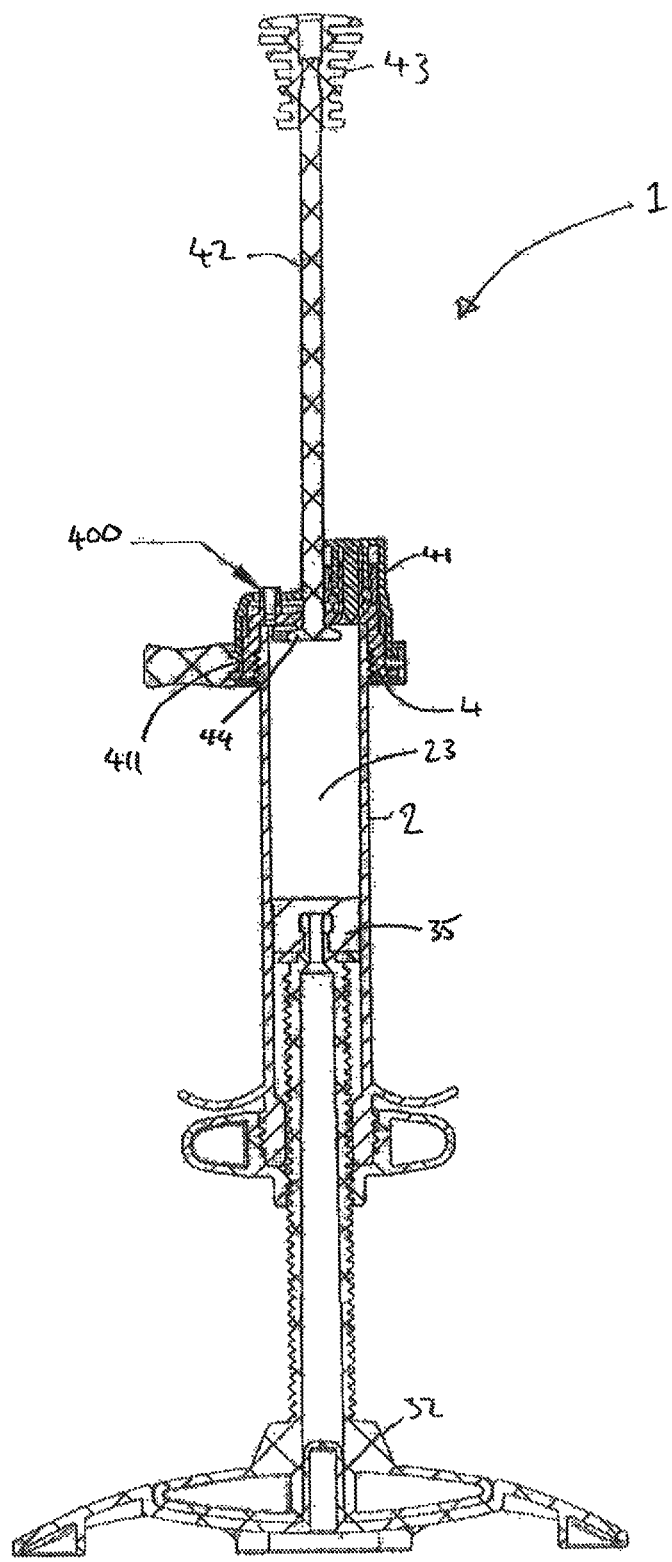
FIG. 6 shows a bone cement mixing and dispensing apparatus in accordance with another embodiment of the present invention.

FIG. 6 shows a complete assembly of a mixing device 1 in accordance with another embodiment of the present invention. The mixing device 1 of FIG. 6 is similar to that of FIG. 1 except that a vacuum port 400 may be included in the outer cap 41 and inner cap 411 so as to be in communication with the chamber 23. A vacuum pump (not shown) may then be received by the vacuum port 400 so as to create a vacuum in the chamber 23.

Figure 7:
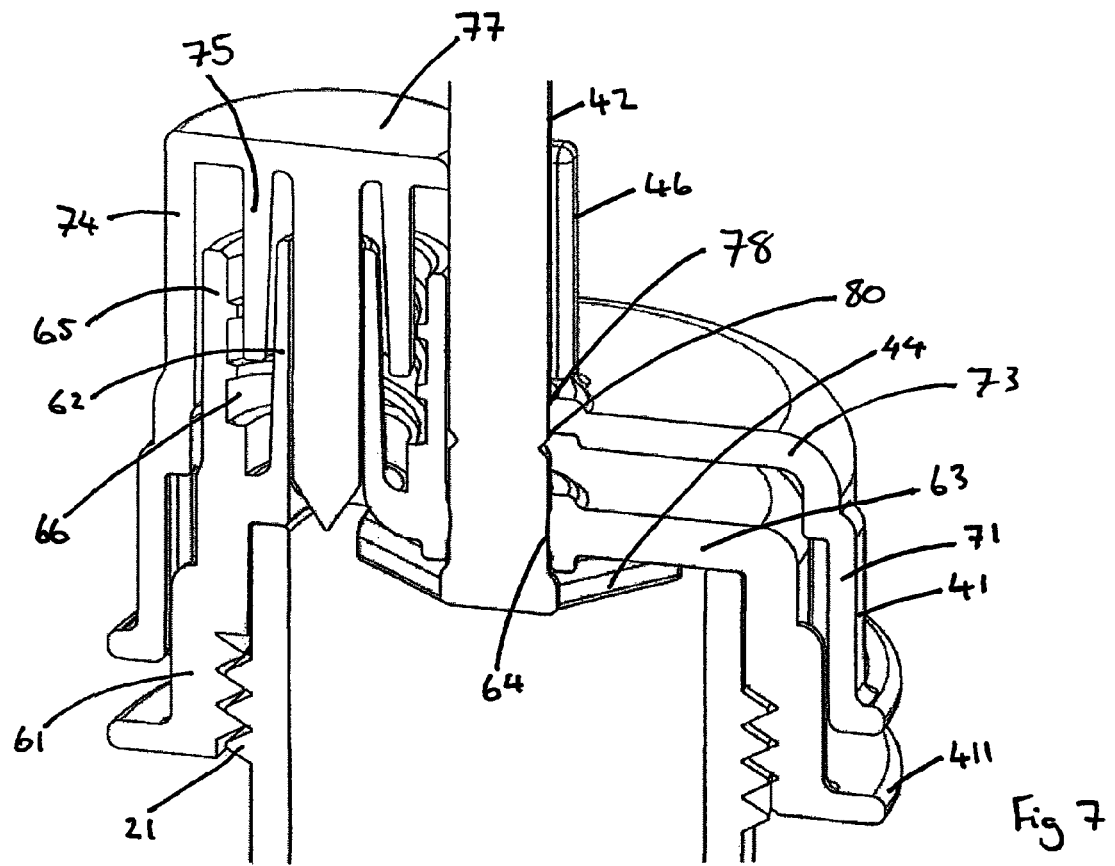
FIG. 7 shows a cross-sectional view of a cap in an open position in accordance with an embodiment of the present invention.
Figure 7A:
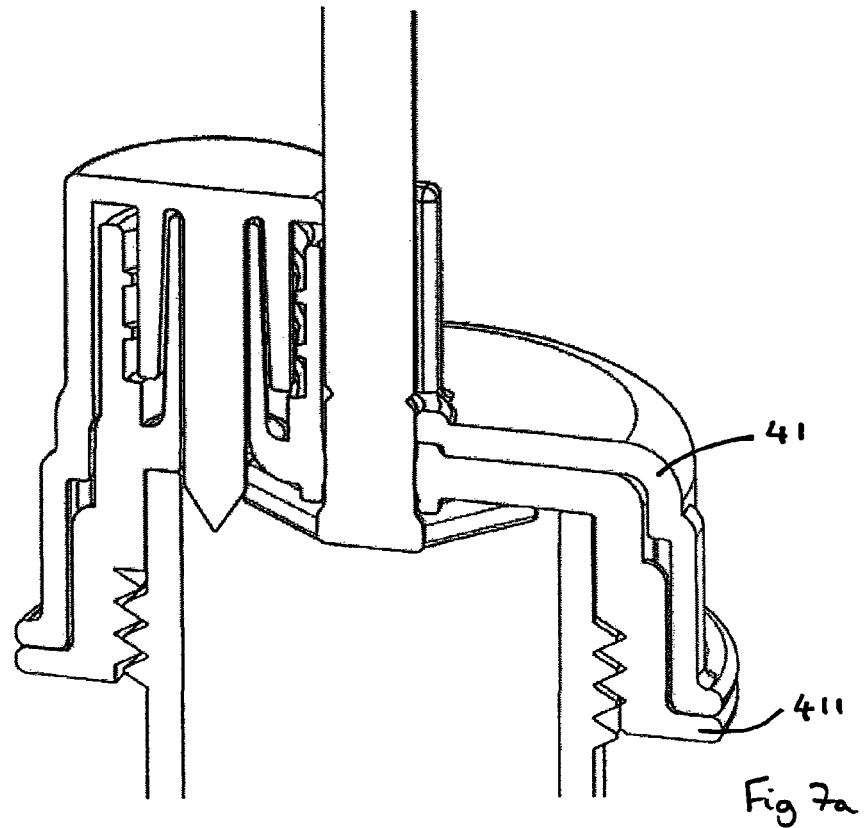
FIG. 7a shows a cross-sectional view of a cap in a closed position in accordance with an embodiment of the present invention.
Figure 7B:
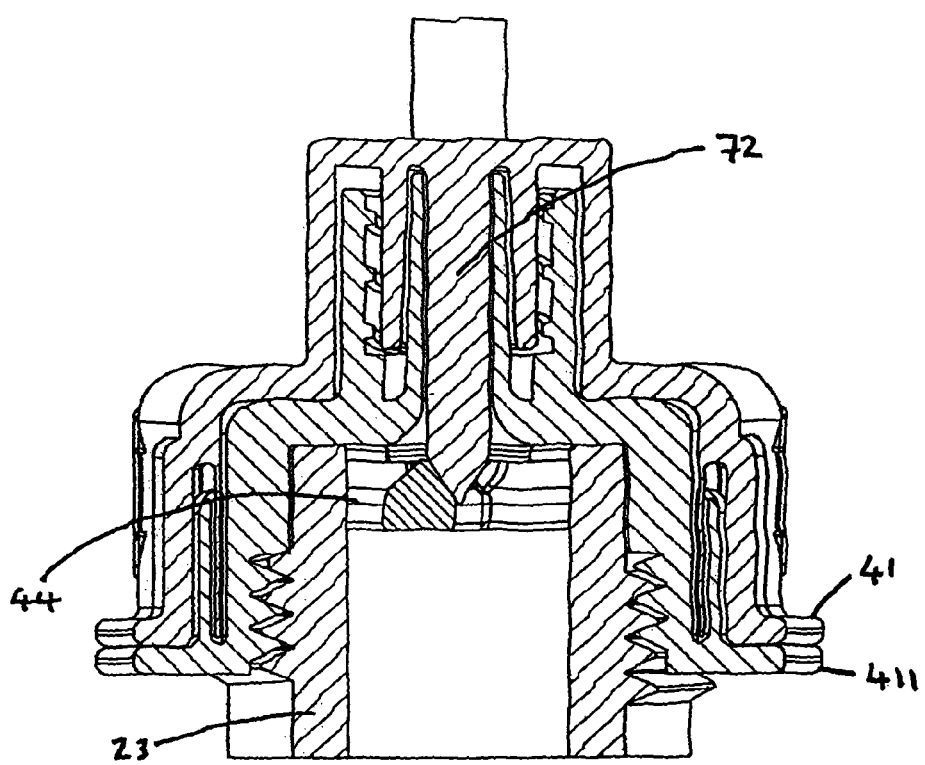

FIGS. 7, 7a and 7b show the inner cap 411, outer cap 41 and rod 42 in more detail. As can be seen in these figures, the inner cap 411 has a side wall 61 extending from an upper wall 63. On the inner surface of the side wall 61, there is provided a screw thread to engage and mate with a screw thread located on the outer surface of the first end 21 of the mixing/dispensing body 2. The upper wall 63 of the inner cap 411 also may include a delivery port 62 extending therefrom towards the outer cap 41 and a circumferential wall 65 located around the delivery port 62 providing a gap 66 therebetween.

The outer cap 41 has a side wall 71 to fit over the side wall 61 of the inner cap 411. The outer cap 41 has an upper wall 73 and a circumferential wall 74 extending therefrom so as to fit over the delivery port 62 and circumferential wall 65 of the inner cap 411. The circumferential wall 74 of the outer cap 41 is closed by an upper surface 77. A protrusion 72 extends from the upper surface 77 towards the delivery port 62 of the inner cap 411 so that the protrusion 72 can be introduced into the delivery port 62. A circumferential wall 75 also extends from the upper surface 77 towards the gap 66 provided between the circumferential wall 65 and the delivery port 62 of the inner cap 411. The circumferential wall 65 includes, on its surface, a luer thread for connection to a luer fitting during the delivery phase.

As shown in FIG. 7, the rod 42 extends through holes 64 and 80 of the inner cap 411 and outer cap 41 respectively. The rod includes a weakened or snap portion 80, which can be formed for example by a slight indent or notch in the material of the rod 42. The outer cap 41 also includes a reinforcing portion 46 which extends from the upper surface 73 of the outer cap 41.

A method of using the outer cap 41 during and after mixing is now described with reference to FIGS. 7, 7a and 7b.

During mixing, the outer cap 41 is raised from the inner cap 411 so as to cover the snap portion 80. The outer cap 41 may then be held in position by a clip 50 (as shown in FIG. 4). The rod 42 can then be moved vertically and/or rotatably by the user to mix the bone cement material in the mixing/dispensing chamber 23 (as shown in FIG. 1). The snap portion is protected against breakage by the outer cap 41. Other means for holding the outer cap 41 in position may also be used.

After the mixing phase, the outer cap 41 is then moved down toward/over the inner cap 411. The protrusion 72 of the outer cap 41 naturally also moves down and engages the paddle portion 44 of the rod 42 and pushes this to the side of the mixing/dispensing chamber 23 to ensure that the paddle portion 44 is not occluding the delivery port 62. In a preferred embodiment, the protrusion 72 is in the form of a spike. The paddle portion 44 may be shaped so as to be engaged by the protrusion 72 to assist in moving the paddle portion 44 to the side of the mixing/dispensing chamber 23.

As can be seen in FIG. 7b, the paddle portion 44 of the rod 42 is moved to the side of the mixing/dispensing chamber 23 such that the paddle portion 44 does not occlude the delivery port 62.

Figure 8:
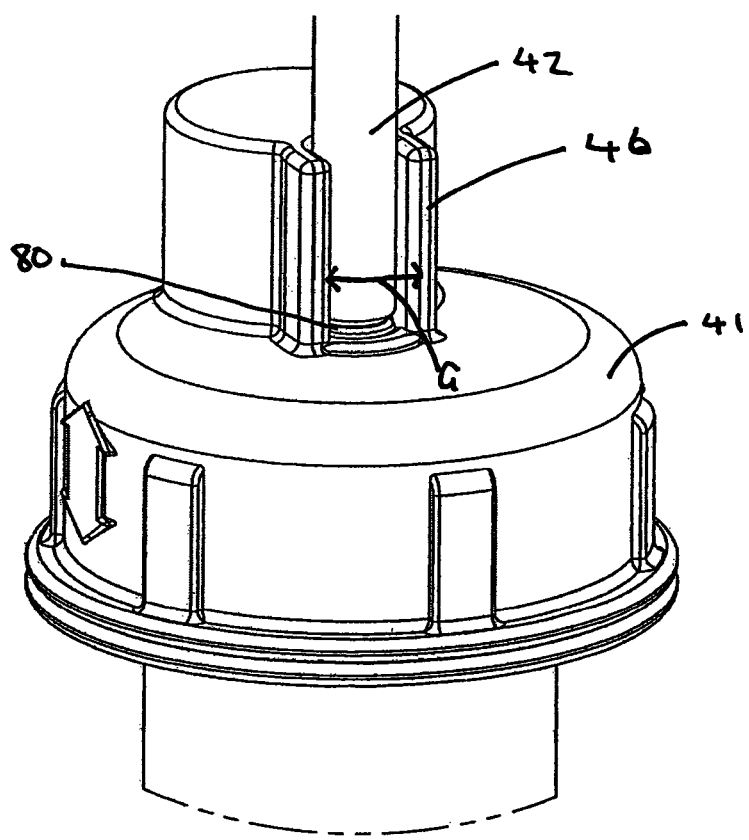
FIG. 8 shows a plan view of the cap shown in FIGS. 6a and 6b.

FIG. 8 shows the outer cap 41 when it is moved down towards, and is fitted over, the inner cap 411. The reinforcing portion 46 has a gap G through which the snap portion 80 is revealed. The user can then "snap" the rod 42 at the snap portion 80 to remove a portion of the rod 42. The paddle portion 44 then remains in hole 64 of the inner cap 411. Due to the paddle portion 44 of rod 42 remaining in hole 64 of the inner cap 411, the paddle portion 44 blocks hole 64 of the inner cap 411 to maintain a closed chamber (as shown in FIGS. 9 and 10).

Figure 9:
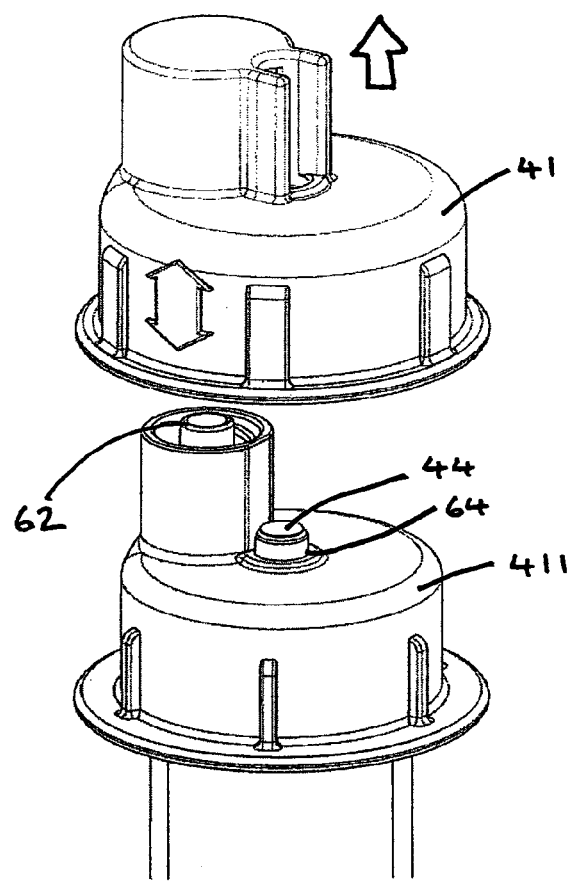
FIG. 9 shows a cap in accordance with another embodiment of the present invention.

FIG. 9 shows that the outer cap 41 can be removed from the inner cap 411 entirely, after the rod 42 has been snapped. As can be seen in this figure, paddle portion 44 remains in hole 64 of the inner cap 411. The outer cap 41 is removed to reveal the delivery port 62.

Figure 10:
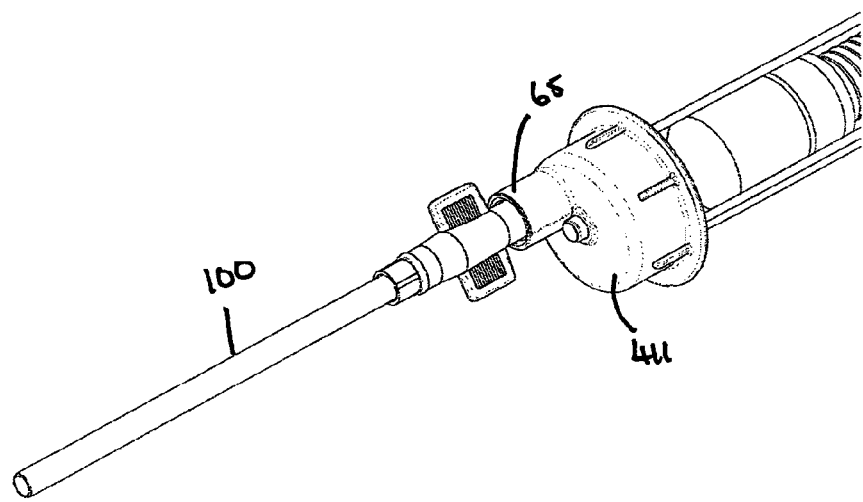
FIG. 10 shows the bone cement mixing and dispensing device of FIG. 1 with a nozzle attached thereto.

FIG. 10 shows that a luer fitting or nozzle 100 can then be connected to the luer thread located on the surface of the circumferential wall 65 of the inner cap 411. The nozzle 100 is then in fluid communication with the mixing/dispensing chamber 23. As mentioned above, paddle portion 44 remains in hole 64 of the inner cap 411.

Figure 11:
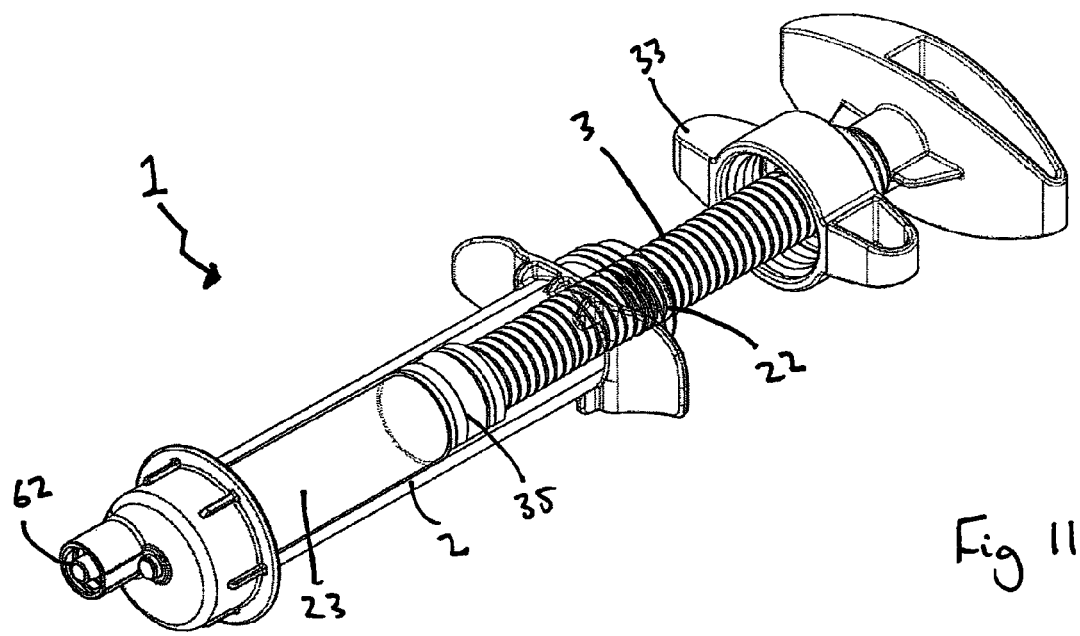
FIG. 11 shows the bone cement mixing and dispensing device of FIG. 1 during the dispensing phase.
Figure 11A:
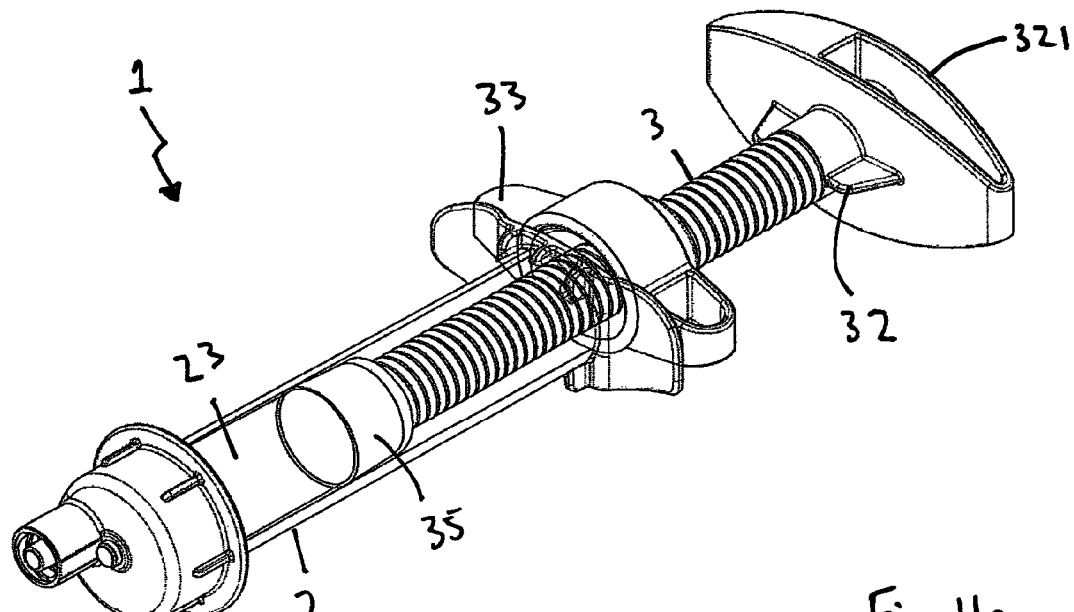
FIG. 11a shows an alternative embodiment of the bone cement mixing and dispensing device of FIG. 1 during the dispensing phase.

FIGS. 11 and 11a show the mixing/dispensing device 1 during the dispensing phase. Once the outer cap 41 has been removed and a nozzle 100 connected so as to be in fluid communication with the mixing/dispensing chamber 23, the bone cement is ready to be delivered to a target site of a patient.

FIG. 11 shows the mixing/dispensing device 1 in one embodiment of the present invention. When the bone cement is ready to be deployed from the mixing/dispensing chamber 23, the user can unscrew the nut 33 from the second end 22 of the mixing/dispensing body 2. The nut 33 can be moved along the screw thread provided on the plunger 3. After unscrewing the nut 33, the plunger 3 can then be axially moved so as to axially move the piston 35. The piston 35 then delivers bone cement through the delivery port 62 and, for example, through a nozzle 100 to the target site.

FIG. 11a shows the mixing/dispensing device 1 in an alternative embodiment of the present invention. When the bone cement is ready to be deployed from the mixing/dispensing chamber 23, the user can rotate the second end 32 of the plunger 3. The second end 32 of the plunger 3 can have a handle or knob 321 attached thereto to assist the user in rotating the plunger 3 through the screw thread provided on the nut 33 to axially move the piston 35. This is particularly useful for viscous bone cement material. Rotating the plunger 3 through the screw thread provided on the nut 33 causes the bone cement to be deployed through the delivery port 62 and, for example, through a nozzle 100 attached thereto.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims.

The invention claimed is:

1. A device for mixing bone cement material, the device comprising:
    a mixing body having a chamber, and wherein the mixing body has an open end;
    a lid arranged to be fitted to the open end;
    means for mixing bone cement material in the chamber, the means for mixing comprising a rod extending through the lid and into the chamber, wherein the rod has a frangible portion;
    said lid comprising a cap moveable to a first position covering the frangible portion of the rod, and to a second position revealing the frangible portion.

2. The device of claim 1, wherein the mixing body has a second open end, and wherein a means for dispensing cement from the chamber is provided at the second open end.

3. The device of claim 2, wherein the means for dispensing cement is a plunger movable by the application of force through the chamber.

4. The device of any preceding claim wherein the means for mixing the bone cement comprises a paddle portion located in the chamber radially extending from the rod.

5. The device of claim 1, said device further comprising means for securing the cap in the first position.

6. The device of claim 5 wherein the means for securing the cap in the first position is a removable clip.

7. The device of claim 3, wherein said device further comprising:
    means for positioning the plunger between the first and the second end of the mixing body to define a volume of the chamber; and
    means for maintaining the position of the plunger so as to maintain the volume of the chamber during mixing.

8. A device for mixing bone cement material, the device comprising:
    a mixing body having a chamber, and wherein the mixing body has a first end and a second end;
    a lid arranged to be fitted to the first end;
    means for mixing bone cement material in the chamber, the means for mixing comprising a rod extending through the lid and into the chamber;
    means for dispensing bone cement material from said mixing body attached to a second end of the mixing body, wherein the means for dispensing the bone cement material is a plunger movable by the application of force through the chamber, said plunger provided to set an adjustable volume in the chamber prior to mixing;
    said device further comprising:
       means for positioning the plunger between the first and the second end of the mixing body to define a volume of the chamber; and
       means for maintaining the position of the plunger so as to maintain the volume of the chamber during mixing, wherein said lid comprising a cap moveable to a first position covering the frangible portion of the rod, and to a second position revealing the frangible portion.

9. The device of claim 7 or 8, wherein the means for positioning the plunger and means for maintaining the position of the plunger comprises:
    a screw thread arranged on an outer surface of the plunger; and
    a nut having a screw thread to be received by the screw thread arranged on the outer surface of the plunger, the nut further having a recess having a screw thread to be received by a screw thread located at the second end of the mixing body.

10. The device of claim 8 wherein the lid comprises:
an inner cap and an outer cap fitted over the inner cap, and wherein the outer cap is movable relative to the inner cap such that, when the outer cap is moved away from the inner cap to the first position, the outer cap covers the frangible portion; and wherein, when the outer cap is moved to the second portion to fit over the inner cap, the frangible portion of the rod is revealed.

11. The device of claim 1, wherein the outer cap has a protrusion that extends through the chamber to engage with the paddle portion when the outer cap is in the second position.

12. A method of mixing bone cement material, said method having the steps of:
providing bone cement components in a mixing chamber of a mixing device;
fitting a lid to an open end of the mixing chamber to close the chamber;
mixing bone cement material using a rod extending through the lid and into the chamber of the mixing device, wherein the rod has a frangible portion; said method characterised by
positioning the lid in a first position so as to reinforce the frangible portion from breakage during mixing;
positioning the lid in a second position so as to reveal the frangible portion; and
snapping the rod at the frangible portion, wherein said lid comprising a cap moveable to a first position covering the frangible portion of the rod, and to a second position revealing the frangible portion.

13. The method of claim 12, wherein the steps of positioning the lid to reinforce the frangible portion comprises:
providing an outer cap and an inner cap on the lid;
moving an outer cap away from an inner cap to a first position.

14. The method of claim 12, wherein the steps of positioning the lid to reveal the frangible portion comprises:
providing an outer cap and an inner cap on the lid;
moving an outer cap to cover the inner cap to a second position.

15. The method of any of claims 12-14, wherein the method further comprises:
positioning a plunger between a first and a second end of a mixing body of the mixing device; and
maintaining the position of the plunger so as to maintain the volume of the chamber during mixing.

16. A method of mixing bone cement material, said method having the steps of:
setting a volume of a chamber of a mixing device with a plunger, said plunger movable through the chamber with the application of force between a first and a second end of the mixing device;
maintaining the position of the plunger so as to maintain the volume of the chamber during mixing;
mixing the bone cement material in the chamber of the mixing device, wherein a lid is coupled to said first end of said mixing device, said lid comprising a cap moveable to a first position covering the frangible portion of the rod, and to a second position revealing the frangible portion.

17. The method of claim 16, wherein the step of setting the volume and maintaining the set volume comprises:
providing a screw thread arranged on an outer surface of the plunger; and
providing a nut having a screw thread to be received by the screw thread arranged on the outer surface of the plunger, the nut further having a recess having a screw thread to be received by a screw thread located at the second end of the mixing body; and
screwing said nut onto the second end of the mixing body.

18. The method of claim 12 or 16, wherein the method further comprises:
dispensing bone cement from the chamber.

* * * * *